United States Patent
Simonov et al.

(10) Patent No.: US 9,744,028 B2
(45) Date of Patent: *Aug. 29, 2017

(54) HAPTIC COMBINATIONS FOR ACCOMMODATING INTRAOCULAR LENSES

(75) Inventors: Aleksey Nikolaevich Simonov, The Haag (NL); Michiel Christiaan Rombach, Breda (NL)

(73) Assignee: Akkolens International B.V., Breda (NL)

( * ) Notice: Subject to any disclaimer, the term of this patent is extended or adjusted under 35 U.S.C. 154(b) by 0 days.

This patent is subject to a terminal disclaimer.

(21) Appl. No.: 13/983,187

(22) PCT Filed: Feb. 3, 2012

(86) PCT No.: PCT/NL2012/050062
§ 371 (c)(1),
(2), (4) Date: Nov. 22, 2013

(87) PCT Pub. No.: WO2012/105843
PCT Pub. Date: Aug. 9, 2012

(65) Prior Publication Data
US 2014/0074233 A1    Mar. 13, 2014

(30) Foreign Application Priority Data
Feb. 3, 2011 (NL) ..................... 2006126

(51) Int. Cl.
*A61F 2/16* (2006.01)
(52) U.S. Cl.
CPC .......... *A61F 2/1613* (2013.01); *A61F 2/1618* (2013.01); *A61F 2/1629* (2013.01); *A61F 2/1632* (2013.01); *A61F 2/1635* (2013.01); *A61F 2002/1681* (2013.01); *A61F 2002/1682* (2015.04); *F04C 2270/0421* (2013.01)

(58) Field of Classification Search
CPC ................. A61F 2/1624; A61F 2/1632; A61F 2002/1682
USPC ....................... 623/6.34, 6.37, 6.38
See application file for complete search history.

(56) References Cited

U.S. PATENT DOCUMENTS

| 6,117,171 | A | 9/2000 | Skottun |
| 7,753,953 | B1 | 7/2010 | Yee |
| 8,377,124 | B2 * | 2/2013 | Hong .................... A61F 2/1632 623/6.32 |

(Continued)

FOREIGN PATENT DOCUMENTS

| EP | 0356050 A1 | 2/1990 |
| WO | 2007016533 A2 | 2/2007 |

(Continued)

*Primary Examiner* — David H Willse
*Assistant Examiner* — Javier Blanco
(74) *Attorney, Agent, or Firm* — The Webb Law Firm

(57) ABSTRACT

A haptic combination comprising at least one optical element adapted to provide at least two optical functions including provision of a fixed optical power and provision of variable optical power. The haptic combination comprises at least a first haptic adapted to provide anchoring and positioning of at least one of the optical elements and at least a second haptic adapted to provide transfer of movement from at least one driving means in the eye to at least one of the optical elements. Movement of the second haptic is independent from movement of the first haptic.

1 Claim, 4 Drawing Sheets

(56) References Cited

U.S. PATENT DOCUMENTS

| | | |
|---|---|---|
| 2007/0108643 A1 | 5/2007 | Zadno-Azizi et al. |
| 2008/0046076 A1* | 2/2008 | Rombach .................... 623/6.34 |
| 2008/0051886 A1 | 2/2008 | Lin |
| 2009/0062912 A1 | 3/2009 | Rombach |
| 2009/0171458 A1 | 7/2009 | Kellan et al. |
| 2009/0228101 A1 | 9/2009 | Zadno-Azizi |
| 2010/0094413 A1 | 4/2010 | Rombach et al. |
| 2010/0121444 A1 | 5/2010 | Ben Nun |
| 2010/0280609 A1 | 11/2010 | Simonov et al. |
| 2010/0324673 A1 | 12/2010 | Nguyen et al. |
| 2011/0125259 A1* | 5/2011 | Klink ................... A61F 2/1627 623/4.1 |
| 2011/0153015 A1 | 6/2011 | Simonov et al. |
| 2011/0282442 A1 | 11/2011 | Scholl et al. |

FOREIGN PATENT DOCUMENTS

| | | | |
|---|---|---|---|
| WO | WO 2008107882 A2 * | 9/2008 | |
| WO | WO 2009051477 A2 * | 4/2009 | ........... A61F 2/1632 |
| WO | 2010089689 A1 | 8/2010 | |
| WO | 2011065833 A1 | 6/2011 | |

* cited by examiner

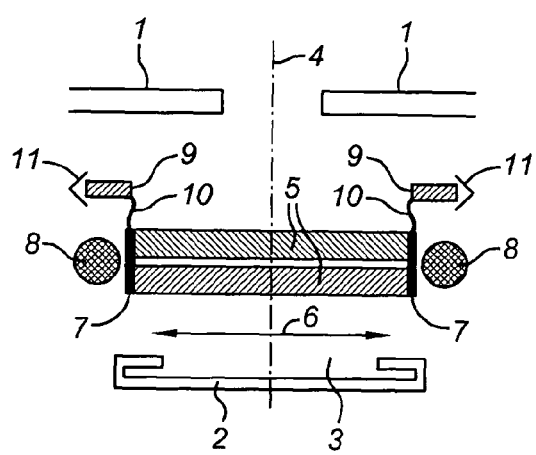
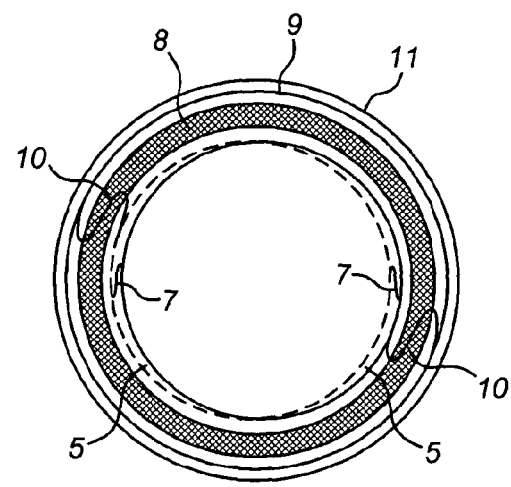
Fig. 1A          Fig. 1B
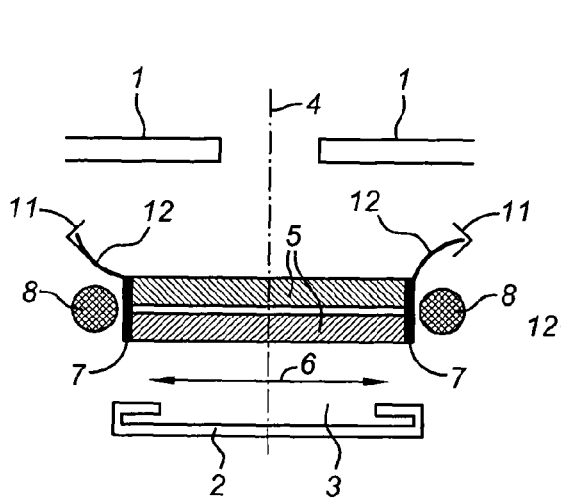
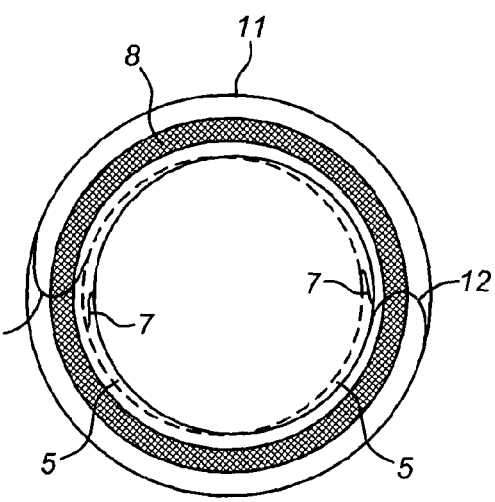
Fig. 2A          Fig. 2B

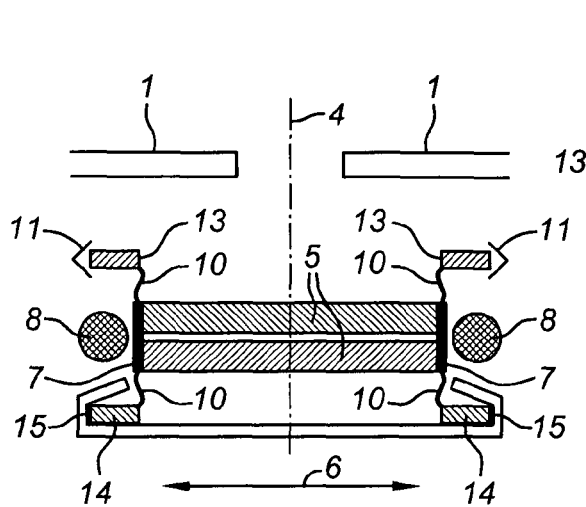
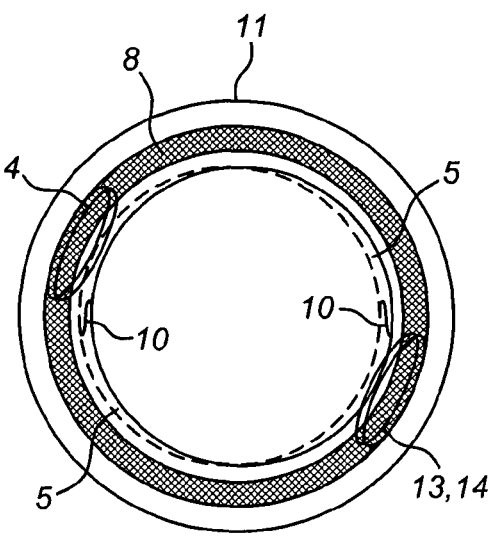
Fig. 3A  Fig. 3B
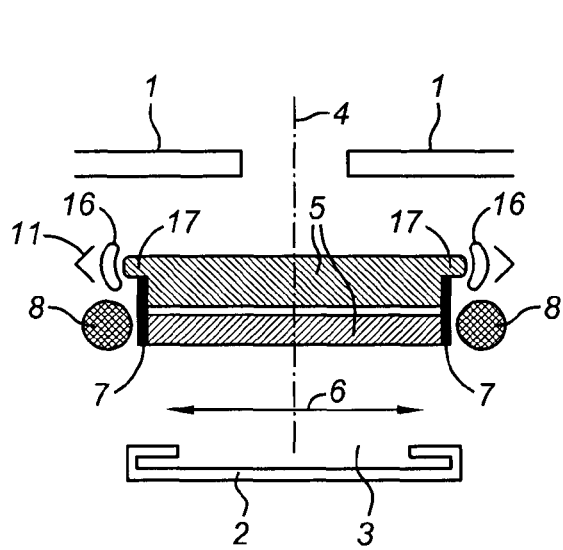
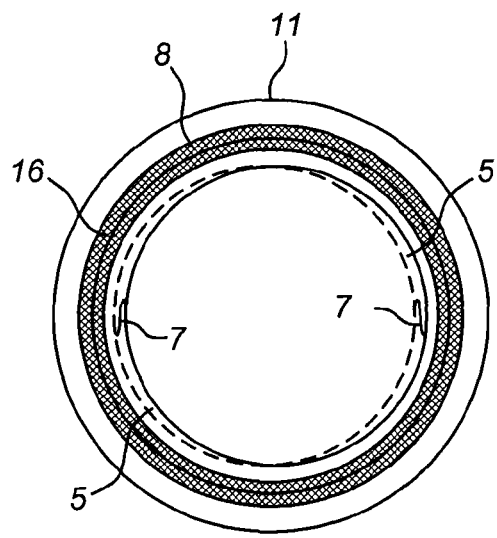
Fig. 4A  Fig. 4B

HAPTIC COMBINATIONS FOR ACCOMMODATING INTRAOCULAR LENSES

CROSS-REFERENCE TO RELATED APPLICATIONS

This application is the United States national phase under 35 U.S.C. §371 of International Application No. PCT/NL2012/050062 filed Feb. 3, 2012, entitled "Haptic Combinations for Accommodating Intraocular Lenses" and claims priority under 35 U.S.C. §119(a)-(d) to The Netherlands Patent Application No. 2006126, filed on Feb. 3, 2011 in The Netherlands Intellectual Property Office, which are hereby incorporated by reference in their entireties.

BACKGROUND OF THE INVENTION

Field of the Invention

Accommodating intraocular lenses are implanted in the human eye as a replacement of the natural lens, correct refraction of the eye and restore accommodation of the eye. The present document discloses haptic combinations for accommodating intraocular lenses.

SUMMARY OF THE INVENTION

The lenses comprise at least one optical element which element is adapted to provide at least two optical functions which functions include provision of fixed optical power to correct refraction of the eye by at least one fixed lens, and, provision of variable optical power to correct accommodation of the eye by at least one variable lens. The haptic combination comprises at least one haptic for focus which haptic is adapted to provide transfer of movement from at least one driving means in the eye to the variable lens. The haptic combination also comprises at least one haptic for position which haptic is adapted to provide anchoring and positioning of the lens in the eye, and, the haptic combination is adapted to provide movement of the haptic for focus independent from movement of the haptic for positioning. So, such haptic combination for accommodating an intraocular lens comprising at least one optical element to provide at least two optical functions including provision of a fixed optical power and provision of variable optical power, with the haptic combination comprising, at least one, first haptic to provide anchoring and positioning of at least one of the optical elements, and, at least one, second haptic to provide transfer of movement from at least one driving means in the eye to at least one of the optical elements, and that movement of the second haptic is independent from movement of the first haptic.

This allows initially to align the position of the optical elements providing the fixed optical power and subsequently to align the optical elements providing the variable optical power.

The second haptic can be adapted to move at least one of the optical elements in the same direction in in which the first haptic is aligned which might result in mutual interference of movements of the haptics. So, to minimize interference, it is preferred that the second haptic is adapted to move at least one of the optical elements in a direction which is different from the direction in which the first haptic is aligned. Herein the term 'moves' is applied to emphasize that this second haptic for focus moves, is largely moveable or driven by, in concert with the driving means in order to transfer said movement from driving means to the optical element proving variable focus during the accommodation process. For the first haptic for positioning the term 'aligned' is applied here to emphasize that this haptic does not transfer the movement of the driving means rather anchors the position of the accommodating lens in the eye and generally remains in a static position. So, the combination of first and second haptics is such that the combination provides both ability to move, to the haptic for focus, as well as ability to align, to the haptic for positioning by providing mechanical independence between the haptic for focus and the haptic for positioning. In the context of the present document movement of the haptic for focus in one direction is a linear movement, forward and backward, along one axis, and any more complex trajectory, such as, for example, rotational movements, in a plane, or screw-type movements, in space, can be described by moving in multiple directions simultaneously.

The direction in which the second haptic is adapted to move at least one of the optical elements can be a direction perpendicular to the optical axis, or, alternatively, can be in the direction of the optical axis, along the optical axis. Such direction of movement is indicated by the type of variable optics which is included in the accommodating lens, which can be optics of which the optical power changes by movement of at least one optical element perpendicular to the optical axis, or, alternatively, can be optics of which the optical power changes by movement of at least one optical element along the optical axis, or, alternatively, can be optics of which the shape of at least one optical element changes with the degree of change in optical power depending on the degree of change in shape, for example change in radius of a lens.

Generally, the second haptic is specifically designed to engage the driving means in the eye for transfer of movement, while the first haptic is specifically designed to engage anchoring points in the eye for anchoring and positioning of the lens, so the embodiments of the haptic for focus generally differ to allow efficient provision of said different functionalities. As stated above the haptic combination can be adapted such that the haptic for focus moves in a direction perpendicular to the optical axis. Generally, the haptic for focus which provide transfer of movement can move along the optical axis, in the direction of the optical axis, but in specific designs of accommodating lenses the haptic for focus moves perpendicular to the optical axis, as in, for example, haptics in accommodating lens designs described in U.S.20080738127 and U.S.200913000145. So, the combination can be adapted such that the haptic for focus moves along at least one axis perpendicular to the optical axis. The haptic for positioning can be aligned along another axis perpendicular to the optical axis, or, alternatively, can be aligned along the same axis as the axis along the haptic for focus moves, but the haptic for positioning is then aligned in a different plane compared to the pane in which the haptic for focus moves.

The connection between the haptic for focus and the haptic for position can be a flexible connection as illustrated, for example, in FIG. 1. The connection should have such flexibility that the movement of the haptic for focus does not interfere with the statically aligned haptic for positioning. Alternatively, a flexible connection the connection between the haptic for focus and the haptic for position can be a largely form-fitting connection as illustrated, for example, in FIG. 4. Such form-fitting connection should be designed sufficiently loose, meaning with sufficient intra connection space, to allow the haptic for focus to move along the range required for the variable lens, but, on the other hand, sufficiently tight to allow the haptic for positioning to properly anchor and position the accommodating lens. Such form fitting connection can be designed such the haptic for positioning embraces the haptic for focus, as illustrated in FIG. 4, or, alternatively, be designed such that the haptic for focus embraces the haptic for positioning.

The haptic combination can include a second haptic which is adapted to be coupled directly to the driving means, for example, the haptic for focus can be coupled to the ciliary muscle of the eye directly. Alternatively, the second haptic can be adapted to be coupled indirectly to driving means, for example, the haptic for focus can be coupled to the capsular bag of the eye. The second haptic is connected to, fused with, at one end, the variable lens and, generally at the opposing end, coupled to, being in contact with, any driving means in the eye driving accommodation, which driving means can be, for example, of mechanical nature, such as the ciliary mass including ciliary muscle, for direct coupling of the ciliary mass to the variable lens, or, alternatively, the capsular bag, for indirect coupling of the ciliary mass to the variable lens, or, alternatively, the iris of the eye, or any other component of the eye which moves in concert with the ciliary muscle, which can also be of hydraulic nature, for example the liquid pressure in the eye which changes along with accommodation. So, the haptic combination can comprises at least one haptic for focus also expressed as the second haptic being adapted to be coupled directly to the driving means, for example, with the haptic for focus coupled to the ciliary muscle of the eye directly. Alternatively, the combination can comprise at least one haptic for focus coupled indirectly to driving means, for example, a haptic for focus coupled to the capsular bag of the eye, which bag is driven by the ciliary muscle via the zonulae, is driven indirectly.

The haptic combination can comprise a first haptic being adapted to provide anchoring of the lens in the sulcus of the eye, or, alternatively, the first haptic may be adapted to provide anchoring of the lens in the capsular bag of the eye.

The haptic combination can comprise at least a second haptic coupled to at least one natural driving means of the eye, for example to the ciliary muscle of the eye or to any other component of the eye which can drive accommodation directly, for example liquid pressure in the posterior chamber of the eye. Alternatively, the haptic combination can comprise at least a second haptic coupled to at least one artificial driving means, for example at least one micro-electro-mechanical system, MEMS, positioned in the eye. Finally the combination may comprise at least a second haptic for focus coupled to at least one combination of at least one natural driving means and at least one artificial driving means. MEMS can include rotational actuators, linear actuators or any other actuators, and, power supply, and, required micro-electronics for controlling the MEMS. In the context of this document, MEMS can also include magnets which are controlled by counter-magnets which counter-magnets can be either implanted in the eye or positioned close to, on to, but outside of, the eye. The MEMS component can include, for example, electrically driven actuators and power supply, with the driving controlled by a controller in the eye or, alternatively, outside the eye. Alternatively, the movement of the ciliary muscle can be amplified, can be leveraged, by using this movement as input for a MEMS which MEMS can be adapted to provide amplification in either force or amplitude of the movement of the ciliary muscle, for example, in cases when the ciliary muscle is not strong enough to sufficiently move the variable lens. The MEMS component, or multiple MEMS components, can also include, at least one, magnet controlled by a controller in the eye or, alternatively, outside the eye, or the MEMS component can include any other combination of, unnatural, components to provide said driving means.

In a preferred embodiment the combination of haptics includes at least a first haptic for positioning in the sulcus, being a position in front of the capsular bag because the sulcus allows for predictability of the lens position in the eye, especially accurate predictability of the position of the lens planes along the optical axis. The sulcus does not change in diameter with accommodation which allows for stable position of the haptics for positioning. Also, the sulcus does not suffer from shrinkage and hardening as does the capsular bag which can decenter intraocular lenses implanted in the capsular bag. Alternatively the combination of haptics includes at least a first haptic for positioning in the capsular bag. In yet another embodiment, the combination of haptics comprises at least a first haptic for position in the sulcus and at least a first haptic for positioning in the capsular bag.

The invention also provides an intraocular accommodating lens comprising at least one haptic combination as disclosed above. The accommodating intraocular lens can further comprise a combination of at least two lenses including at least one lens providing variable optical power to correct accommodation of the eye which variable lens comprises at least two optical elements, at least one of which is movable relative to the other in a direction perpendicular to the optical axis, wherein the optical elements have such a form as to result in a lens with different optical power at different relative positions of the optical elements with the degree of movement of the optical element depending on the degree of force exerted onto the second haptics by the driving means. Such optical arrangements for intraocular lenses are described in detail in, for example, U.S.20080738127, U.S.2010094413 and WO2011065833.

Alternatively, the accommodating intraocular lens can further comprise a combination of at least two optical elements of which at least one element is movable relative to the other in the direction of the optical axis, wherein the optical elements have such a form as to result in a lens with different optical power at different relative positions of the optical elements along the optical axis with the degree of movement of the optical element depending on the degree of force exerted onto the second haptics by the driving means. Such optical arrangements for intraocular lenses are described in detail in, for example, U.S.2010324673, U.S.2009228101, WO2007016533 and U.S.2007108643.

Alternatively, the accommodating intraocular lens can further comprise a combination of at least one optical element one optical element comprising at least one variable lens providing variable optical power to correct accommodation of the eye provided by a change in shape in the direction of the optical axis with the degree of said change in shape depending on the degree of force exerted onto the second haptics by driving means. Such optical arrangements for intraocular lenses are described in detail in, for example, U.S.2011153015 and U.S. Pat. No. 7,753,953 and U.S.2011282442.

BRIEF DESCRIPTION OF THE DRAWINGS

Subsequently the present invention will be elucidated with the help of the accompanying drawings, wherein show:

FIG. 1a: a cross sectional view of a first embodiment of the invention;

FIG. 1b: an axial view of the haptic depicted in FIG. 1a;

FIG. 2a: a cross sectional view of a second embodiment of the invention;

FIG. 2b: an axial view of the haptic depicted in FIG. 2a;

FIG. 3a: a cross sectional view of a third embodiment of the invention;

FIG. 3b: an axial view of the haptic depicted in FIG. 3a;

FIG. 4a: a cross sectional view of a fourth embodiment of the invention;

FIG. 4b: an axial view of the haptic depicted in FIG. 4a;

DESCRIPTION OF THE INVENTION

Figure 5A:
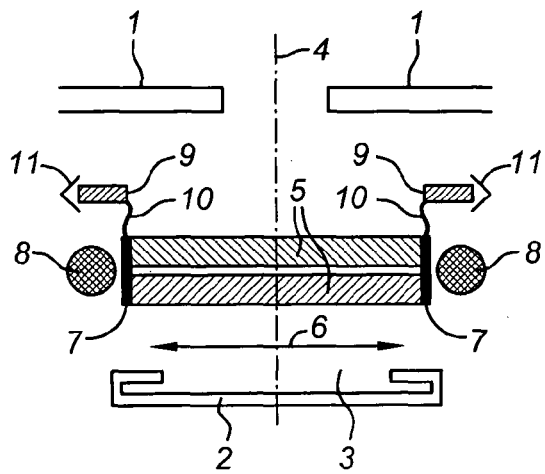
FIG. 5a: a cross sectional view of a fifth embodiment of the invention in the rest position.

FIGS. 1a and 1b show a lens with haptic combination for positioning in the sulcus. The variable lens schematically positioned in the posterior chamber of the eye behind the iris 1 and the capsular bag 2 from which the natural lens is removed through the capsullorhexis, 3, with central optical axis, 4, comprises, in this example, a combination of at least two optical elements, 5, which, in this particular example, are optical elements in an arrangement such that the elements can be shifted relative to each other in a direction indicated by arrow 6 perpendicular to the optical axis, as in, for example, U.S.20080738127, which example is set forth in FIGS. 1-4, with the note that the inventions are not limited to only such optical arrangements. The haptic combination comprises at least one haptic 7 for focus, coupled to driving means 8 in the eye, in this example the ciliary muscle of the eye, and at least one haptic 9 for position, being connected to the haptic 7 for focus, or, alternatively, connected to any components of the optical elements by a flexible connection, 10, and which haptic for position is coupled to at least one anchoring point in the eye, 11, which anchoring point can be, for example, the sulcus of the eye. Right panel, top view: In this example the haptic for position is a circular loop design haptic in top view, 9, for other components refer to the descriptions above.

FIGS. 2a and 2b show a lens with C-loop haptics for positioning. The variable lens, with central optical axis, 4, comprises, in this example, a combination of at least two optical elements, 5, which can be shifted relative to each other in a direction perpendicular to the optical axis, 6. The haptic combination comprises at least one haptic for focus, 7, and at least one haptic for position, in this example a C-loop type haptic, 12, positioned, in this example, in the sulcus, 11, connected to the haptic for focus, or, alternatively, to any components of the optical elements, with accommodation driven by driving means, 8, in this example, by the ciliary muscle. Right panel, top view: Schematic of lens with C-loops in top view. For explanation of components refer to descriptions above.

FIGS. 3a and 3b depict a lens with multiple haptics for positioning. The variable lens, with central optical axis, 4, comprises, in this example, a combination of at least two optical elements, 5, which can be shifted relative to each other in a direction perpendicular to the optical axis, 6. The haptic combination comprises at least one haptic for focus, 7, and at least two sets of haptics for position, in this example an anterior set of haptics for position, 13, positioned in, for example, the sulcus, 11, and a posterior set, 14, positioned, in this example, at an anchoring point posterior of the ciliary mass, 15, for example in the capsular bag, with all haptics for position connected to the haptic for focus, 7, or, alternatively, to any other component connected to of the optical elements, by flexible connections, 10. Right panel, top view: For explanation of components refer to descriptions above.

FIGS. 4a and 4b show a lens with haptics for positioning embracing the optical elements and the haptics for focus. The variable lens, with central optical axis, 4, comprises, in this example, a combination of at least two optical elements, 5, which can be shifted relative to each other in a direction perpendicular to the optical axis, 6. The haptic combination comprises at least one haptic for focus, 7, and at least one form fitting haptic for position, 16, which embraces, is not connected to, other components of the lens, by the loose form fitting connection, with the haptic for focus being fitted, in this example, with a flange, 17, to achieve such form fitting construction in combination with the haptics for position. Right panel, top view: For explanation of components refer to descriptions above.

Figure 5B:
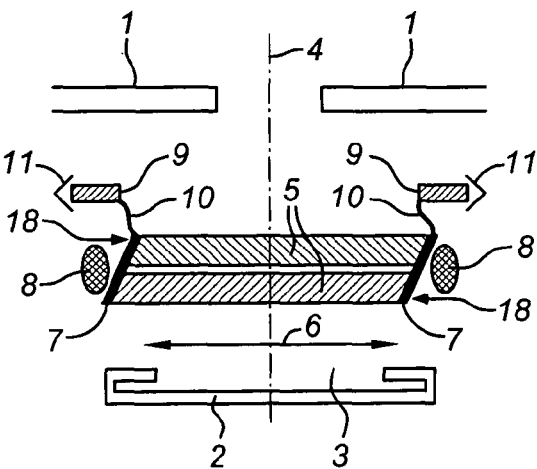
FIG. 5b: a view similar to FIG. 5a in the accommodated position.

FIGS. 5a and 5b show a lens with an optical arrangement similar to the above FIGS. 1-4, but wherein the features of U.S.20080738127 are applied. The variable lens comprises at least two optical elements and with the degree of optical power depending on the degree of movement as represented by reference number 18 of at least one element relative to the other element in a direction perpendicular to the optical axis with FIG. 5a showing the lens in a resting state, resulting in an emmetrope eye and FIG. 5b showing the lens in an accommodated state, with the movement provided by force exerted by driving means on the second haptics. Herein the same reference numbers are used as in FIGS. 1-4.

Figure 6A:
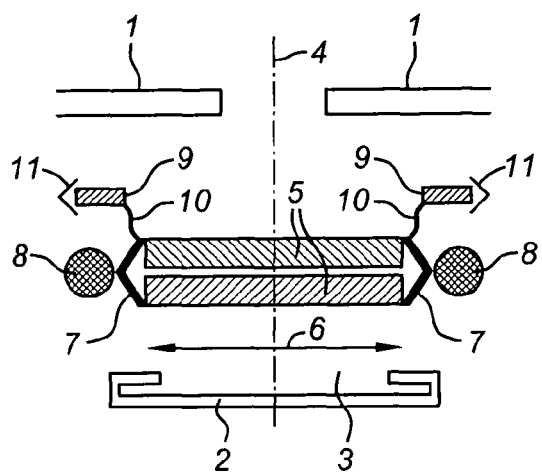
FIG. 6a: a cross sectional view of a sixth embodiment of the invention in the rest position.
Figure 6B:
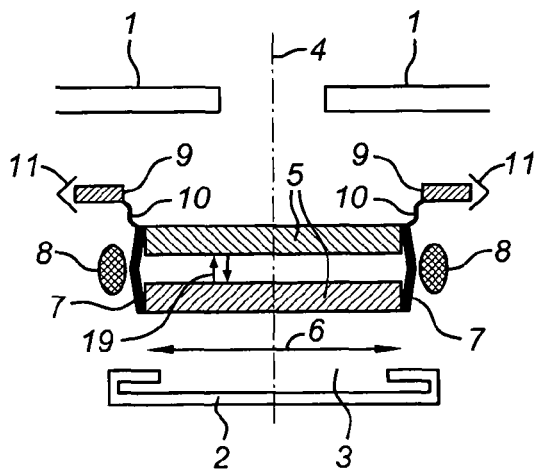
FIG. 6b: a view similar to FIG. 6a in the accommodated position.

FIGS. 6a and 6b show a lens with an optical arrangement similar to the above FIGS. 1-4, but wherein features of U.S.2010324673 are applied. The variable lens comprises at least two optical elements and with the degree of optical power depending on the degree of movement, 19, of at least one element relative to the other element in a direction along the optical axis, with FIG. 6a showing the lens in a resting state, resulting in an emmetrope eye and FIG. 6b showing the lens in an accommodated state, with the movement provided by force exerted by driving means on the second haptics. Herein the same reference numbers are used as in FIGS. 1-4.

Figures 7A, 7B:
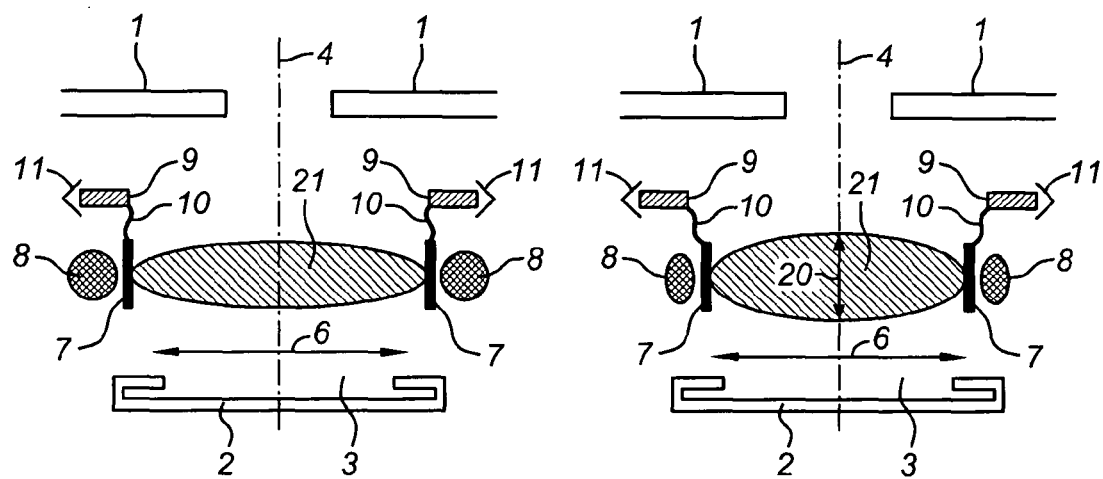
FIG. 7a: a cross sectional view of a seventh embodiment of the invention.
FIG. 7b: a view similar to FIG. 7a in the accommodated position.

FIGS. 7a and 7b show a lens with an optical arrangement similar to the above FIGS. 1-4, but wherein features of U.S.2011153015 are applied. The variable lens comprises one optical element 21 and with the degree of optical power depending on the degree of change in shape 20, of said element, with FIG. 7a showing the lens in a resting state, resulting in an emmetrope eye and FIG. 7b showing the lens in an accommodated state, with the change in shape of the optical element 20 provided by force exerted by driving means on the second haptics. Herein the same reference numbers are used as in FIGS. 1-4.

All documents to which the present document refers are included in the present documents by said references. It will be clear that numerous variations can be applied to the embodiments discussed above within the scope of the claims.

The invention claimed is:

1. An accommodating intraocular lens (IOL) with variable optical power and having an optical axis, the intraocular lens comprising:
   an anterior optical element and a posterior optical element of which at least one is movable relative to the other in a direction perpendicular to the optical axis, wherein each of the anterior and posterior optical elements have a shape that they exhibit, in combination, different optical powers at different positions of one optical element relative to the other optical element in the plane perpendicular to the optical axis, and
   a first set of haptics and a second set of haptics,
   wherein the first set of haptics are positioning haptics comprising sulcus-engaging surfaces adapted to provide anchoring and positioning of the optical elements in an eye and adapted to be directly coupled to the sulcus of the eye, the first set of haptics located an axial distance from the anterior and posterior optical elements,
   wherein the second set of haptics are haptics for moving comprising ciliary muscle-engaging surfaces adapted and dimensioned to be directly coupled to the ciliary muscle of the eye, the second set of haptics adapted to provide a transfer of movement from the ciliary muscle to at least one of the posterior optical element and the anterior optical element, the second set of haptics connects the anterior optical element and the posterior optical element and extends in a first direction relative to the optical axis in a rest position, wherein the second set of haptics is located a radial distance from the optical elements such that the second set of haptics tilts relative to the optical axis in an accommodated position and mutually shifts the anterior and posterior optical elements in opposite directions relative to each other along a direction perpendicular to the optical axis, wherein the degree of movement of the optical elements depends on the degree of force exerted onto the second set of haptics by the ciliary muscle,
   wherein movement of the second set of haptics is independent from movement of the first set of haptics, and wherein the second set of haptics is adapted to move at least one of the optical elements in a direction in which is different from the direction in which the first set of haptics positions one of the optical elements, and
   wherein the first and the second set of haptics are connected by a flexible connection extending in a direction parallel to the optical axis.

* * * * *